United States Patent
Saber et al.

(10) Patent No.: US 10,376,355 B2
(45) Date of Patent: Aug. 13, 2019

(54) ARTIFICIAL DIAPHRAGM HAVING INTELLIGENT NANOMAGNETIC PARTICLES FOR TREATMENT OF DIAPHRAGMATIC PARALYSIS

(71) Applicants: Tina Saber, Irvine, CA (US); Poona Saber, Scottsdale, AZ (US); Mahmood Mirhoseini, Germantown, WI (US); Sassan Saber, Tehran (IR); Aria Manasheri, Tehran (IR)

(72) Inventors: Tina Saber, Irvine, CA (US); Poona Saber, Scottsdale, AZ (US); Mahmood Mirhoseini, Germantown, WI (US); Sassan Saber, Tehran (IR); Aria Manasheri, Tehran (IR)

(*) Notice: Subject to any disclaimer, the term of this patent is extended or adjusted under 35 U.S.C. 154(b) by 0 days.

(21) Appl. No.: 15/902,772

(22) Filed: Feb. 22, 2018

(65) Prior Publication Data
US 2018/0177584 A1 Jun. 28, 2018

Related U.S. Application Data

(60) Provisional application No. 62/528,539, filed on May 7, 2017.

(51) Int. Cl.
*A61F 2/08* (2006.01)

(52) U.S. Cl.
CPC ........ *A61F 2/08* (2013.01); *A61F 2002/0894* (2013.01); *A61F 2210/009* (2013.01); *A61F 2250/0001* (2013.01)

(58) Field of Classification Search
CPC ...... A61F 2250/0001; A61F 2002/0894; A61F 2210/009; A61M 1/10
USPC ....................................... 623/14.13
See application file for complete search history.

(56) References Cited

U.S. PATENT DOCUMENTS

| | | | |
|---|---|---|---|
| 5,509,888 A * | 4/1996 | Miller | A61B 17/12 128/DIG. 25 |
| 2007/0098622 A1* | 5/2007 | Nakayama | B01J 27/22 423/447.3 |
| 2012/0323318 A1* | 12/2012 | Yusuf | A61M 1/1053 623/3.11 |

* cited by examiner

*Primary Examiner* — Yashita Sharma
(74) *Attorney, Agent, or Firm* — Barry Choobin; Patent 360

(57) ABSTRACT

The embodiments herein relate to an artificial diaphragm made up of a plurality of plates having nanoparticles which move to-and-fro creating a movement similar to a natural diaphragm. The embodiments herein provide an artificial diaphragm that can mimic diaphragmatic movements of a natural diaphragm in a human body. The artificial diaphragm is embedded with intelligent nanomagnetic particles which is used for treatment of diaphragmatic paralysis.

8 Claims, 1 Drawing Sheet

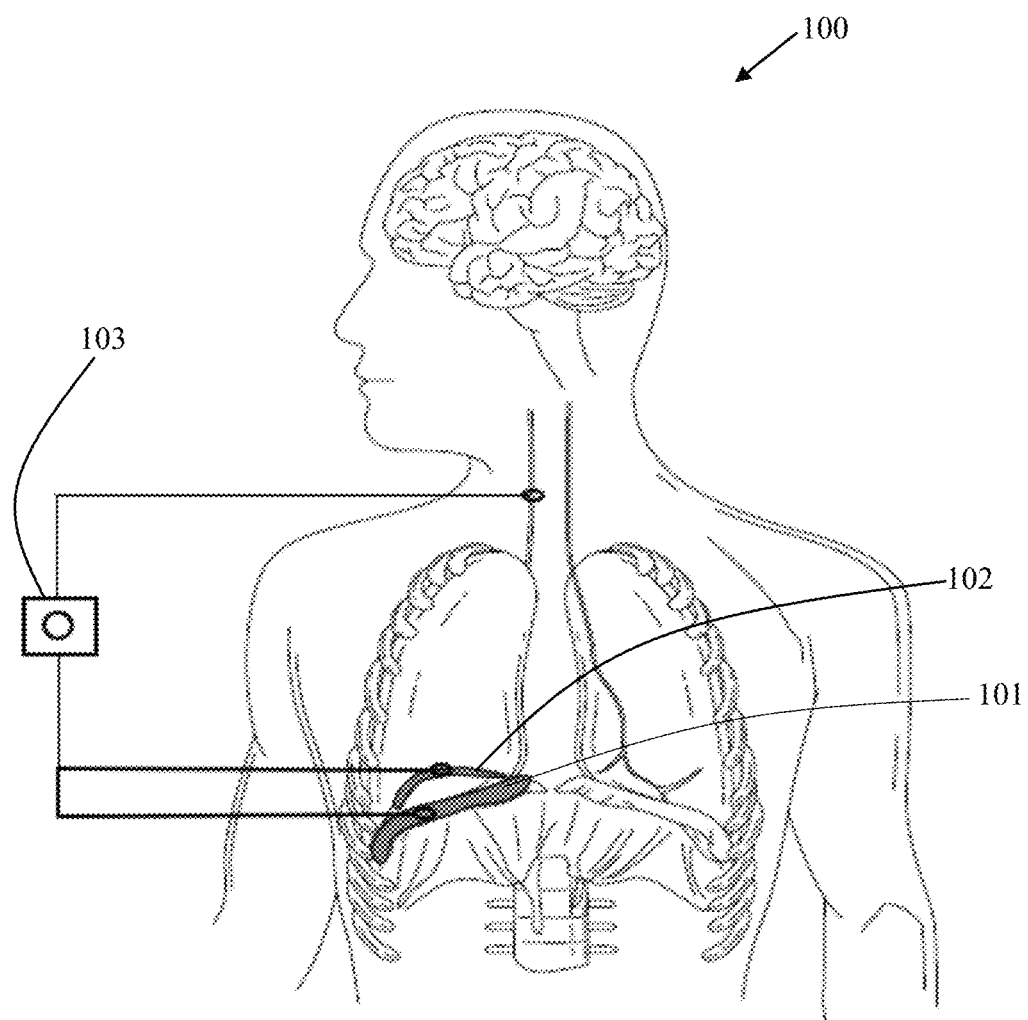

ARTIFICIAL DIAPHRAGM HAVING INTELLIGENT NANOMAGNETIC PARTICLES FOR TREATMENT OF DIAPHRAGMATIC PARALYSIS

BACKGROUND

Technical Field of Invention

The embodiments herein generally relate to diaphragms and particularly to artificial thoracic diaphragms for use in conditions such as diaphragmatic paralysis. The embodiments herein more particularly relate to artificial diaphragm comprising intelligent nanomagnetic particles embedded in diaphragmatic plates.

Description of Related Art

Breathing action consist of ventilator pump, including chest wall muscles; diaphragms and accessory intercostal and extra thoracic muscles. Diaphragms are right and left dome-like musculo-tendinous structures at the floor of chest which separate abdomen from the thorax.

Lungs are suspended in the thorax under a negative pressure of −5 cm of water. Normally during inspiration, diaphragms contracture makes domes move downward and get flat form, so increases the vertical volume of the thorax by about 20%, and contracture of the external intercostals muscles increases anterior or sternum to spine volume as well. With normal atmospheric pressure, this condition makes intrathoracic more negative pressure to −7.5 cm. So lungs expand and air flows inward and gas exchange between oxygen and carbon dioxide can take place in the alveoli. Inspiration costs minimum work and minimum metabolic energy. Whereas expiration phase is passive and elastic property makes chest wall relax and diaphragms go back to their main dome shape and air gets out of lungs, spending no energy. Activity of inspiratory muscles especially diaphragms are vital for life.

The movement of the diaphragm must be effective in any situation at day-time, either at rest or any level of activity, by adapting itself with increasing ventilation needs like sport, exercise, stress and even disease conditions, and otherwise at sleep time it must be autonomic. So, ventilation is self-organized, means that it regulates itself to any situation. This auto-regulation is managed by respiratory centre in the brainstem, medulla oblongata and pons, which receive neural, chemical and hormonal signals to control the rate and depth of diaphragm movement via two right and left phrenic nerves, which origin from cervical C 3-4-5 motor nerve roots and run on front the scalene muscles through thorax and go down on the anterior wall of pericardium and finally innervate two hemi diaphragms.

Like any other striated muscle, respiratory muscles need energy of mitochondrial oxidation metabolism. During this pathway acetylcholine binds to nicotinic receptors and releases calcium to cytoplasm which activates the ATP-ase to convert ATP to ADP, and then shortening the myosin fibers of muscle makes contraction.

In conditions of diaphragm fatigue or dysfunction, there is a threat to the life of the individual. Hence there is a need for an extra push to move the diaphragm just a little for a regular breath. After couple of months, if dyspnea in patient doesn't improve and paralysis doesn't recover, some strategies can be advised to restore its deficit movement.

The oldest procedure is surgical plication of diaphragm which is suggested for unilateral paralysis. In this technique, thin diaphragm gets flat with no normal nerve or muscle function, but expanded lungs improve better mechanism. The other technique is specialized neck micro-surgery to rescue the compressed nerve or implant it, if vital forces of nerve or diaphragm have been preserved. The diaphragmatic pacing is indicated when phrenic nerve and diaphragm muscles are intact, e.g. central paralysis. Electrodes are implanted around the neck phrenic nerves and an external radio wave source generates signals. Pacing needs months to achieve a full effect by an atrophic diaphragm. But if after paralysis, diaphragms muscles undergo atrophy, pacemaker alone is not effective.

Hence there is a need to develop an artificial diaphragm having intelligent nanomagnetic particles for treatment of diaphragmatic paralysis. There is a need to develop an artificial diaphragm which mimics diaphragmatic movement which in turn increases the volume of the thorax vertically thus increasing lung volume and improving respiration.

The above-mentioned shortcomings, disadvantages and problems are addressed herein, as detailed below.

SUMMARY OF THE INVENTION

The primary object of the embodiments herein is to provide an artificial diaphragm that can mimic diaphragmatic movements.

Another object of the embodiments herein is to provide an artificial diaphragm embedded with intelligent nanomagnetic particles for treatment of diaphragmatic paralysis.

Yet another object of the embodiments herein is to provide an artificial diaphragm that works on nanotechnology.

Yet another object of the embodiments herein is to provide an artificial diaphragm that is inserted and attached to assist as a substitute for the paralyzed diaphragm, and a wireless chargeable microchip to control the movement of the diaphragm.

The embodiments herein provide an artificial diaphragm having intelligent nanomagnetic particles for treatment of diaphragmatic paralysis. The artificial diaphragm comprises at least two polymeric plates. The one of the plates is fixed and the second one is mobile. The artificial diaphragm further comprises nanocoils, nanomagnets, a pacemaker, and a micro-controller. The nanocoils are present in one of the plates. The nanocoils are 1 to 1000 nm sized magnetic coils. The nanomagnets are embedded in the other plate. The pacemaker is r-wave.

According to an embodiment herein, the at least two special polymeric structured plates (P.T.S.).

According to an embodiment herein, the two plates attract and repel each other once an electric current is passed through them.

According to an embodiment herein, the rate of respiration is adjusted corresponding to the pacemaker, unilaterally or bilaterally.

According to an embodiment herein, the fixed plate is plan is shape.

According to an embodiment herein, the mobile plate is concave in shape.

According to an embodiment herein, the magnetic field of coils on each sheet are paralleled, and magnetic field of second sheet are paralleled too.

According to an embodiment herein, the polymeric plates are embedded with nanomagnets.

According to an embodiment herein, when the magnetic field of two sheets are similar, they repel each other. and when their fields are inversed, by different polarity they will be attracted to toward each other.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide an artificial diaphragm made up of a plurality of plates having nanoparticles which move to-and-fro creating a movement similar to a natural diaphragm. The embodiments herein provide an artificial diaphragm that can mimic diaphragmatic movements. The artificial diaphragm is embedded with intelligent nanomagnetic particles which is used for treatment of diaphragmatic paralysis.

According to an embodiment herein, an artificial diaphragm having intelligent nanomagnetic particles for treatment of diaphragmatic paralysis. It comprises at least two special polymeric structured plates (P.T.S.), wherein one of the plates is fixed and the second one is movable. Both fixed and movable plates comprise special nano-coils (A.M.S.) while polymeric structured plates embedded with nanomagnets. The two plates attract and repel each other once an electric current is passed through them. If both plates have the same polarity charge, the plates repel each other while if both the plates have opposite charges, the plates attract each other causing movement of the diaphragm. The rate of respiration is adjusted automatically. This is triggered by microcomputer. The action of attraction or repelling mimics diaphragmatic movement and the volume of the thorax increases vertically and increases lung volume and improves respiration. The at least two polymeric plates and the phrenic nerve are controlled by an implanted microcomputer either unilaterally or bilaterally.

FIG. 1 is a diagrammatic representation of the artificial diaphragm having intelligent nanomagnetic particles for treatment of diaphragmatic paralysis, according to an embodiment herein. With respect to FIG. 1, the artificial diaphragm 100 having intelligent nanomagnetic particles for treatment of diaphragmatic paralysis comprises at least two polymeric plates 101 and 102. One of the plates 101 is fixed and the second one 102 is mobile. Nanocoils are present in one of the plates. The nanocoils are 1 to 1000 nm sized magnetic coils. The nanomagnets are embedded in the other plate and a pacemaker is also provided. The pacemaker is r-wave. The artificial diaphragm is triggered by a microcontroller 103. The at least two special polymeric structured plates (P.T.S.). The two plates attract and repel each other once an electric current is passed through them. The rate of respiration is adjusted corresponding to the pacemaker, unilaterally or bilaterally. The fixed plate is plan is shape. The mobile plate is concave in shape. The magnetic field of coils on each sheet are paralleled, and magnetic field of second sheet are paralleled too. The polymeric plates are embedded with nanomagnets. When the magnetic field of two sheets are similar, they repel each other. and when their fields are inversed, by different polarity they will be attracted to toward each other.

The design of an artificial diaphragm is based on nanotechnology, it is inserted and attached to assist or substitute for the paralyzed diaphragm. Intelligent nano-magnetic coils are embedded into two polymeric plates. An implanted micro-computer controls these two plates and the phrenic nerve, either unilaterally or bilaterally. One of the plates is fixed and the second one is movable. Both fixed and moveable magnetic plates consist special polymeric structures embedded with nano-magnets coils. Passing electric current through the two plates causes them to attract to each other and come together or repel each other and move in opposing directions. If both plates have similar polar charge, they repel each other. And if they have opposite charges they attract each other causing movement of the diaphragm. The rate of respiration is adjusted automatically and triggered by micro-computer. The action of attraction or repelling in moving the plates mimics diaphragmatic movement and the volume of the thorax increases vertically and increases lung volume and improve respiration.

Experimental Details

In fatigue conditions energy supplement gets inadequate versus demands of ventilation and breathing work increases, so patient complains of dyspnea and gradually falls in morbidity. Healthy one can perform a ventilator volume of about 7 liters per minute and can increase it to about 5 times upon the forced conditions mentioned above. In hyperinflation conditions like COPD and Asthma diaphragm will already be flat as expiration situation with no effective movement, so patient will breathe rapid and shallow and non-effective.

Paralysis of diaphragms may happen unilateral or bilateral. Unilateral paralysis occurs due to phrenic nerve injury or interruption. During an open thorax surgery or cervical vertebra injury, a tumor invasion, mediastinal diseases, neuro-myosis problems (amyotrophic lateral syndrome), infection diseases, post viral neuropathy (e.g. post-polio syndrome), congenital eventration, neck irradiation, Guillain-Barre syndrome and other unknown complications. Moreover, cooling the heart during cardiac surgery can temporary damage phrenic nerve or diaphragm, leading to paralysis, which usually occurs in about 2% of cases and on left side.

Bilateral paralysis, usually occurs by sever cord injury, thoracic trauma, sever myopathy, multiple sclerosis, hypo thyroidism, acid maltose deficiency, Lupus syndrome, malnutrition, general neuro- muscular disorders, and often unknown.

Manifestations: With paralysis the whole mechanical and biochemical act of respiration gets severely disturbed and diaphragm muscles undergo atrophy and patient uses abdominal and ancillary muscles of respiration. The pathophysiology of process makes patient experiment diaphragm orthopnea (due to hydrostatic pressure of abdomen and decreasing of vital capacity). Symptoms would be relief on upright position. Dyspnea develops by excessive daytime Somnolence and anxiety and morning headache. It progresses to hypoxia, hypercapnia, right heart failure, respiratory failure and complicates by lung atelectasis, gastro-oesophageal reflux due to thoracic pressure reduction and increased pressure of abdomen, recurrent pneumonia. Dyspnea sometimes occurs in immersion due to increasing of abdomen pressure. On physical examination prominent activity of accessory muscles of inspiration (intercostal and scalene). Patient would be relief in upright position.

Excluding conditions are obstructive lung diseases, congestive heart failure, thrombo-embolic diseases and pulmonary arterial hypertension. Paralysis not due to spinal cord injury may improve spontaneously over period of months to years.

Traumatic and non-traumatic paralysis appears by the diaphragm weakness to seriously dysfunction. It may resolve within 6 to 12 months but may develop and even stay for many years even for life time. So, patient will require non-invasive positive airway pressure or may make patient be dependent to ventilator machines.

Sleep disorder breathing is a high-risk condition, especially the REM disorder which compared to typical OSA, it may be central hypopnea with more sever desaturation because of respiratory muscle fatigues due to mechanical disadvantage.

Diagnosis: is often incidentally. Usually it depends on discovering abnormal movement of diaphragms, by biphasic respiratory chest x ray or fluoroscopy or ultrasonography.

By chest x-ray imaging in unilateral paralysis, during inspiratory negative thoracic pressure, disordered diaphragm will paradoxically elevate. And in bilateral paralysis, minimal or absent movement of both diaphragms will be founded.

Fluoroscopy is a gold examination to find either a paradoxical movement of diaphragm in inspiration and sometimes diminished or absent of diaphragm movement.

Ultrasonography also can show the abnormal movements, besides can measure the changes of diaphragm thickness between TLC and FRC phase, which less than 20% change indicates the paralysis.

Magnetic Stimulation of neck phrenic nerve with no response of diaphragm trans-pressure.

Electromyography evaluates the neuromuscular response of diaphragm. Phrenic nerve stimulation perform by supraclavicle electrodes and diaphragm response will be recorded on the 7 and 8 intercostal level.

Pulmonary function tests may reveal pattern of restrictive lung disease, reduction in Total Lung Capacity. Forced Vital Capacity, diminished Forced 1st second Expiratory Volume, but preserved FEV1/FVC. And diminished Maximal Inspiratory Pressure (especially in supine position). Trans-diaphragmatic pressure by inserting two balloon catheters into gastric and esophageal space (Pgn. Pps) elevates during normal inspiration but shows no difference in diaphragmatic Paralysis.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims.

We claim:

1. An artificial diaphragm having intelligent nanomagnetic particles for treatment of diaphragmatic paralysis comprises:
    at least two polymeric plates, wherein one of the plates is fixed and the second one is mobile;
    nanocoils, wherein nanocoils are present in all of the at least two polymeric plates, wherein the nanocoils are 1 to 1000 nm sized magnetic coils;
    nanomagnets, wherein the nanomagnets are embedded in all of the at least two polymeric plates; and
    a pacemaker, wherein the pacemaker is r-wave; and
    a micro-controller.

2. The artificial diaphragm according to claim 1, wherein the at least-two polymeric plates are special polymeric structured plates.

3. The artificial diaphragm according to claim 1, wherein the atleast two polymeric plates attract and repel each other once an electric current is passed through them.

4. The artificial diaphragm according to claim 1, wherein a rate of respiration is adjusted corresponding to the pacemaker, unilaterally or bilaterally.

5. The artificial diaphragm according to claim 1, wherein the fixed plate is planar in shape.

6. The artificial diaphragm according to claim 1, wherein the mobile plate is concave in shape.

7. The artificial diaphragm according to claim 1, wherein a magnetic field of coils on each plate are paralleled, and magnetic field of second plate are paralleled too.

8. The artificial diaphragm according to claim 1, wherein when a magnetic field of two plates are similar, they repel each other, and when their fields are inversed, by different polarity they will be attracted to toward each other.

* * * * *